May 9, 1939. E. E. GLOMSTEAD Re. 21,076

SANITARY NAPKIN

Original Filed Feb. 16, 1932

Inventor
Edwin E. Glomstead
By Fisher, Clapp, Soans & Pond Attys.

Reissued May 9, 1939

Re. 21,076

UNITED STATES PATENT OFFICE 21,076

SANITARY NAPKIN

Edwin E. Glomstead, Menasha, Wis., assignor to International Cellucotton Products Company, Chicago, Ill., a corporation of Delaware Original No. 1,857,854, dated May 10, 1932, Serial No. 593,360, February 16, 1932. Application for reissue July 6, 1937, Serial No. 152,265

5 Claims. (Cl. 128—290)

The principal object of this invention is to provide a sanitary napkin of superior form fitting characteristics, that is to say, to provide a sanitary napkin in which the pad element is so formed that its end portions will have a decided tendency to maintain a normal flat condition and to fit snugly against the body without protruding sufficiently to cause any anxiety to the wearer that the presence of the napkin will be detectable by reason of any bulge or the like in the dress of the person. The improved construction is of particular advantage when tight fitting dresses are worn, but the increased comfort of a smooth and close fitting sanitary napkin renders the improvement advantageous and desirable without regard to the style of clothing worn.

Other objects and advantages of the invention will be understood by reference to the following specification and accompanying drawing in which is illustrated a sanitary napkin embodying a selected form of the improved construction.

Figure 1:
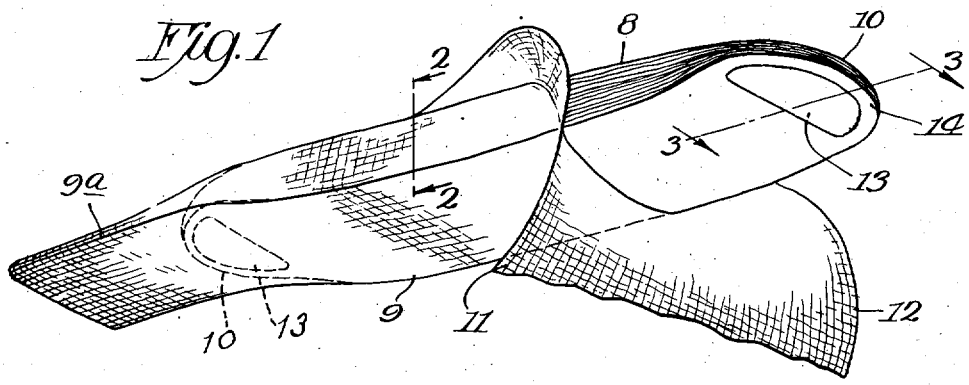
Fig. 1 is a perspective, a portion of the wrapper being unfolded to disclose the interior construction.
Figure 2:
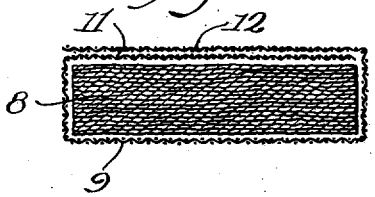
Fig. 2 is a section on the line 2—2 of Fig. 1.

Referring now to the drawing, the improved sanitary napkin therein illustrated includes a pad element 8 which is surrounded by a gauze or like textile material wrapper 9. The pad element 8 is elongated and has rounded ends as indicated at 10 and the gauze wrapper is also elongated and folded longitudinally around the pad element so that its side marginal portions 11 and 12 overlap the top side of the pad. The gauze wrapper extends considerably beyond the ends of the pad element 8 to form attachment flaps such as indicated at 9a.

The pad element 8 is preferably formed of a plurality of relatively superposed layers or sheets of cellulose wadding, i. e., crepe paper. Such a pad has a very high capacity for absorption and it has been found to be very soft and flexible so that it is well-adapted for sanitary napkin purposes.

According to the present invention, the end portions of the pad element are treated so as to stiffen the end portions transversely and preferably to taper the normal thickness of the pad to a comparatively thin end. This result may be effected by compressing or compacting the ends of the pad in areas spaced slightly inwardly from the end edge of the napkin as indicated at 13.

The pressure required to effect the desired result may vary with different materials and with different runs of any one material, such as crepe paper, wherefore it is impracticable to definitely specify in terms of pounds per square inch the minimum pressure required. However, it may be stated that to attain the object of the invention in its preferred form, the pressure should be sufficient to cause the compacted area to become hard or firm to the touch, i. e., substantially uncompressible between the fingers, and to cause the compacted area to be sharply defined from the uncompressed portion.

Figure 3:
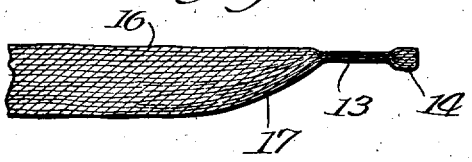
Fig. 3 is a section on the line 3—3 of Fig. 1.

As clearly shown in Fig. 3, a marginal edge portion 14 it not directly compressed but is nevertheless reduced in thickness to a marked extent as an incident to the compacting of the area 13. Hence, said marginal portion 14 of the pad retains a certain degree of fluffiness or softness. The softness of said margin constitutes the same a cushion at the edge of said compacted area, whereby said edge, which obviously is relatively hard and harsh, is prevented from causing chafing of the wearer.

By compressing the end portions of the pad in the manner just described, the sheets or layers of paper which form the pad are united, in effect, welded together so that they will resist separation and relative slippage both longitudinally and transversely. In this way the area 13 is also stiffened so that it tends to retain its normal flat condition.

Figure 6:
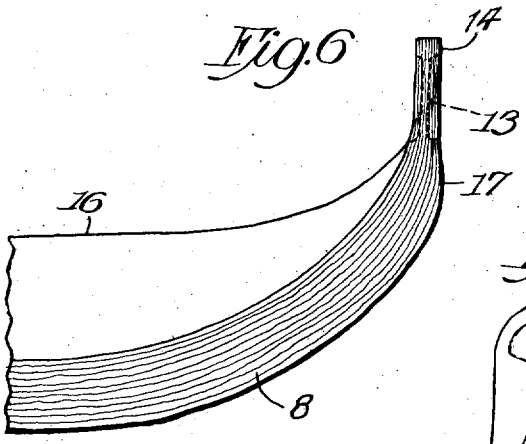
Fig. 6 is a side elevation of one end portion of the pad element.
Figure 5:
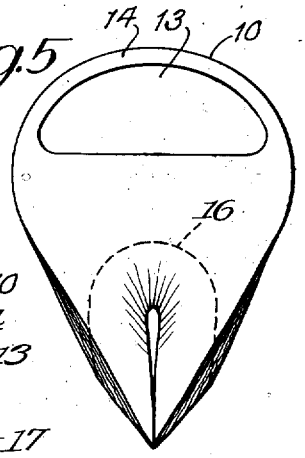
Fig. 5 is an end elevation of the pad element when in the condition illustrated in Fig. 4.
Figure 4:
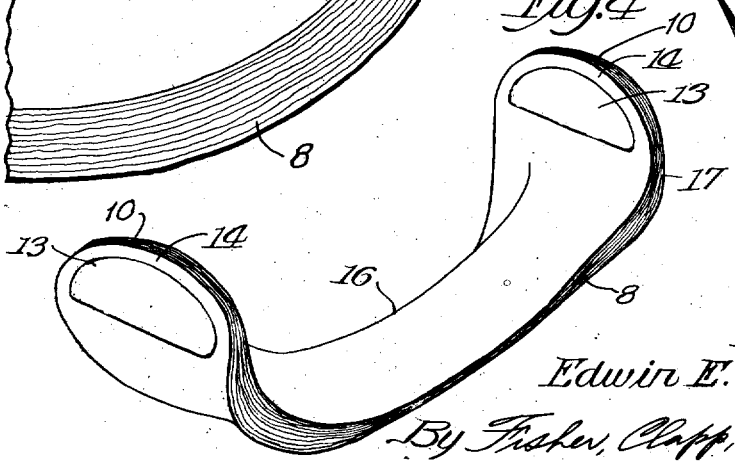
Fig. 4 is a perspective of the pad element alone bent to substantially the shape which it takes when worn.

When a napkin embodying the described pad construction is applied, the body portion of the pad element intermediate its ends is folded longitudinally and downwardly so as to present a smooth, convex top surface 16 and the opposite ends of the pad are turned upwardly to lie flat against the body. The compressed and stiffened area 13 serves to maintain the end portions substantially flat so as to avoid any bulging effect at the ends of the pad. As evident from an inspection of Fig. 3, the compacting of the ends of the pad element is preferably effected in such a manner as to maintain the top 16 of the pad substantially flat throughout its length and so as to effect the tapering of the thickness of the pad at its ends principally on the bottom or outside of the pad element. Hence, when the pad assumes the condition illustrated in Figs. 4, 5 and 6, the tapered portion 17 of the pad assumes a position in which it does not project materially beyond the plane of the extreme end portion of the pad. Hence, bulging does not occur at a point spaced below the extreme end of the pad. The thinness of the extreme ends of the pad also serves to avoid any bulging effect of such extremities.

When a napkin is applied, it is ordinarily suspended from a belt or undergarment to which it is secured at each end either by means of a single buckle, safety pin or other fastening means, thus concentrating the upward draft or pull mainly along the centerline of the gauze wrapper. This centerline pull has a tendency to crease or wrinkle the end portions of the pad, more or less in continuation of the fold of the intermediate portion of the pad. This tendency is effectively resisted by the stiffened area 13 so that the body hugging characteristic of the pad ends is insured.

Changes may be made in the described construction without departing from the spirit of the invention, the scope of which should be determined by reference to the following claims, the same being construed as broadly as possible consistent with the state of the art.

I claim:

1. A sanitary napkin comprising an absorbent pad which is disintegrable in water, an area adjacent but spaced inwardly from an end of the pad being compacted sufficiently to form an area of permanently reduced thickness and of such stiffness that it tends to maintain the adjacent end portions of the pad in substantially flat condition when the napkin is worn, the marginal portion of said pad intermediate said compacted area and the adjacent end of the pad being reduced in thickness from the normal thickness of the pad as an incident to the compacting of said area, but said marginal portion retaining sufficient softness to constitute a non-chafing cushion at the edge of said compacted area.

2. A sanitary napkin comprising an absorbent pad formed of a plurality of relatively superposed plies of crepe paper, an area adjacent but spaced inwardly from an end of the pad and located substantially in the plane of one face of the pad being compacted sufficiently to, in effect, weld said plies together to prevent relative shifting thereof and to form a hardened area of permanently reduced thickness and of such stiffness that it tends to maintain the adjacent end portions of the pad in substantially flat condition when the napkin is worn, the marginal portion of said pad intermediate said compacted area and the adjacent end of the pad being reduced in thickness from the normal thickness of the pad as an incident to the compacting of said area, but said marginal portion retaining sufficient softness to constitute a non-chafing cushion at the edge of said compacted area.

3. A sanitary napkin comprising an absorbent pad element which is disintegrable in water and a wrapper of textile material, the pad element having an area in an end portion thereof compacted sufficiently to produce an area of compression permanently reduced in thickness relative to the normal thickness of the pad, one surface of said area being substantially offset relative to the normal surface of the pad and there being an angularly disposed surface portion intervening between and connecting said surface of the compressed area with said normal surface of the pad, said area serving to stiffen such end portion sufficiently to main the same in substantially flat condition when the napkin is applied.

4. A sanitary napkin comprising an absorbent pad element and a wrapper of textile material, the pad element being formed of superposed plies of crepe paper and having an area in an end portion thereof compacted sufficiently to produce an area of compression wherein the plies are mechanically united strongly enough to prevent relative shifting thereof and wherein the thickness is permanently reduced, said area of compression serving to stiffen said end portion sufficiently to maintain the same in substantially flat condition when the napkin is applied, one surface of said area being substantially offset relative to the normal surface of the pad and there being an angularly disposed surface portion intervening between and connecting said surface of the compressed area to the normal surface of the pad.

5. A sanitary napkin comprising an absorbent pad formed of a plurality of relatively superposed plies of crepe paper, an area of the pad adjacent but spaced inwardly from an end thereof being compacted sufficiently to mechanically unite said plies in said area to prevent relative shifting of said plies and to form a hardened area of permanently reduced thickness and of such stiffness that said area tends to maintain the adjacent end portion of the pad in substantially flat condition when the napkin is worn, the marginal portion of said pad intermediate said compacted area and the adjacent end of the pad being reduced in thickness from the normal thickness of the pad as an incident to the compacting of said area but said marginal portion retaining sufficient softness to constitute a non-chafing cushion in the edge of said compacted area.

EDWIN E. GLOMSTEAD.